United States Patent
Pijl (10) Patent No.: US 11,100,781 B2
(45) Date of Patent: Aug. 24, 2021

(54) MONITORING A SUBJECT

(71) Applicant: Lifeline Systems Company, Framingham, MA (US)

(72) Inventor: Marten Jeroen Pijl, Eindhoven (NL)

(73) Assignee: Lifeline Systems Company, Framingham, MA (US)

( * ) Notice: Subject to any disclaimer, the term of this patent is extended or adjusted under 35 U.S.C. 154(b) by 0 days.

(21) Appl. No.: 16/909,546

(22) Filed: Jun. 23, 2020

(65) Prior Publication Data

US 2020/0410837 A1 Dec. 31, 2020

(30) Foreign Application Priority Data

Jun. 26, 2019 (EP) .................................. 19182674

(51) Int. Cl.
*G08B 1/00* (2006.01)
*G08B 21/04* (2006.01)
(Continued)

(52) U.S. Cl.
CPC .......... *G08B 21/0446* (2013.01); *A61B 5/112* (2013.01); *A61B 5/1117* (2013.01); *G08B 21/043* (2013.01); *G08B 25/016* (2013.01)

(58) Field of Classification Search
CPC .................................... G08B 1/00; A61B 1/00
See application file for complete search history.

(56) References Cited

U.S. PATENT DOCUMENTS

2011/0230791 A1\* 9/2011 Ten Kate ............... G08B 29/22
600/595
2016/0220153 A1 8/2016 Annegarn
(Continued)

FOREIGN PATENT DOCUMENTS

WO 2012146957 A1 11/2012
WO 2015091581 A1 6/2015

OTHER PUBLICATIONS

Zijlstra, Wiebren et al "Assessment of spatio-temporal gait parameters from trunk accelerations during human walking", Science Direct, Gait and Posture, vol. 18, 2003, pp. 1-10.
International Search Report and Written Opinion dated Sep. 18, 2020 for International Application No. PCT/EP2020/066848 Filed Jun. 18, 2020.

*Primary Examiner* — Shirley Lu
(74) *Attorney, Agent, or Firm* — Honigman LLP; Grant Griffith (57) ABSTRACT

According to an aspect, there is provided a computer-implemented method of monitoring a subject. The method comprises, following detection of a first fall by the subject and a revocation of a fall alert for the first fall due to detecting the subject has stood up after the first fall, obtaining first measurements of movement of the subject; determining a first value of at least one mobility characteristic of the subject from the obtained first movement measurements; determining if the mobility of the subject has degraded after the first fall based on the first value of the at least one mobility characteristic and a second value of the at least one mobility characteristic, wherein the second value is determined from second movement measurements obtained prior to the first fall; and in response to determining that the mobility of the subject has degraded after the first fall, performing a fall alert action in respect of the first fall. A corresponding apparatus and a computer program product are also provided.

18 Claims, 2 Drawing Sheets

(51) Int. Cl.
*A61B 5/11* (2006.01)
*G08B 25/01* (2006.01)

(56) References Cited

U.S. PATENT DOCUMENTS

2016/0321903 A1 11/2016 Smits
2019/0099114 A1 4/2019 Mouradian

* cited by examiner

MONITORING A SUBJECT

CROSS-REFERENCE TO PRIOR APPLICATIONS

This application claims the benefit of European Patent Application No. 19182674.2, filed Jun. 26, 2019 which is incorporated by reference herein.

FIELD OF THE INVENTION

The invention relates to monitoring a subject, and in particular to a computer-implemented method, apparatus and computer program product for monitoring a subject.

BACKGROUND OF THE INVENTION

Falls are common among older adults. A fall is an event which typically results in a person impacting with and coming to rest on the ground or floor. In an estimated 20-30% of cases, falls lead to mild or severe injuries and may result in visits to an emergency department. A person lying on the ground or floor for a long time after a fall may be detrimental to the person, and therefore it is of importance to get help as fast as possible after a fall. Personal Emergency Response Systems (PERS) can enable people to signal for help by pressing a help button that is worn as a pendant around the neck or on the wrist. When the person presses their help button, they can be connected to a help provider (sometimes referred to as a "Personal Response Agent") (e.g. in a call centre) via an in-home communicator. The help provider may then assist the person in the event of an emergency, and/or offer the person help or assistance. The assistance provided by the help provider may include one or more of providing verbal assistance, alerting a neighbour, friend or family member of the person, or calling emergency services.

In addition to a help button, certain PERS devices can contain one or more sensors, such as an accelerometer and air pressure sensor, for enabling falls to be automatically detected. Algorithms that use the sensor signal(s) as input may be used to automatically trigger an alert in case a fall is detected. This may result in help being obtained for the person more quickly, particularly if the person is not able to press the help button (e.g. the person is unconscious) or forgets to press the button. These algorithms typically determine values for one or more features from the sensor signals (e.g. an impact magnitude, a change in altitude, etc.) and determine whether a fall has occurred on the basis of those feature values.

In some PERS devices, an alert is only triggered or initiated if the person of the PERS device does not stand up within a predetermined time period following a detected fall (sometimes referred to as the "revocation period"). If it is detected by the PERS device that the person has stood up following the fall in this revocation period, an alert may be cancelled or revoked. As a result, a number of false alarms which the person of the PERS device may be confronted with will be reduced (for example, where a false alarm is triggered by an everyday event that may resemble a fall from the perspective of one or more sensors).

Presently, the revocation of a fall alert is based on the detection that the person has stood up after the detected fall. However, the fact that a person has stood up following a fall does not necessarily mean that the person is uninjured. Although the person could press their help button in order to receive assistance, it is considered that people are often reluctant or unwilling to do this, even in the case that a person has been injured. It has been found that people with PERS devices that enable falls to be automatically detected report many more falls than people with a non-fall detection enabled PERS device, with many falls being unreported as a result of the person not pressing their help button following a fall.

Therefore there is a need for techniques that facilitate assistance being requested for a person in case they are injured following a fall.

SUMMARY OF THE INVENTION

The techniques proposed herein provide an approach that makes use of mobility-related measurements to provide a more fine-grained revocation analysis of an alert related to a detected fall.

In particular, if a fall alert is revoked due to the subject standing up within a revocation period, mobility-related measurements can be obtained. From these measurements, it can be determined if there are noticeable changes to the subject's mobility following the fall, in comparison to the subject's mobility prior to the fall. Any changes may be indicative of potential injury, disorientation or confusion of the subject as a result of the fall (or indeed, as a cause of the fall), and so a fall alert requesting assistance for the subject may still be triggered, or the subject may be prompted or reminded to trigger an alert indicating that they require assistance.

These techniques facilitate assistance being requested for a person in case they are injured following a fall.

These techniques can be used both with dedicated devices for evaluating movement (e.g. a PERS device, a fall detector, a walking detector, etc.), and other devices that can be programmed or configured to evaluate movement (e.g. a smartphone or smartwatch).

According to a first aspect, there is provided a computer-implemented method of monitoring a subject. The method comprises, following detection of a first fall of the subject and a revocation of a fall alert for the first fall due to detecting the subject has stood up after the first fall, obtaining first measurements of movement of the subject; determining a first value of at least one mobility characteristic of the subject from the obtained first movement measurements; determining if the mobility of the subject has degraded after the first fall based on the first value of the at least one mobility characteristic and a second value of the at least one mobility characteristic, wherein the second value is determined from second movement measurements obtained prior to the first fall; and in response to determining that the mobility of the subject has degraded after the first fall, performing a fall alert action in respect of the first fall. Thus, this aspect provides that assistance can still be requested for the subject following a revoked fall alert if the movements of the subject show a degradation following the fall.

In some embodiments the step of performing a fall alert action comprises issuing an alert to request assistance for the subject. In this way assistance can be automatically requested for the subject. In these embodiments an alert can comprise at least one of an audible alarm, placing a call to a call centre, emergency service or nominated recipient, or sending data to a call centre, emergency service or nominated recipient.

In alternative embodiments, the step of performing a fall alert action, comprises issuing a prompt to the subject to trigger an alert that the subject has fallen and/or that the subject requires assistance. In this way the decision on whether to request assistance remains with the subject, but the prompt may encourage the subject to request assistance.

In some embodiments the step of determining if the mobility of the subject has degraded after the first fall comprises determining the difference between the first value of the at least one mobility characteristic and the second value of the at least one mobility characteristic; and determining that the mobility of the subject has degraded if the difference between the first value of the at least one mobility characteristic and the second value of the at least one mobility characteristic is more than a threshold amount.

In some embodiments the second value for the at least one mobility characteristic represents a normal value for the at least one mobility characteristic. Thus, the first aspect determines if the subject's movements after the fall have degraded relative to the subject's typical movement ability.

In some embodiments the method further comprises, prior to detection of the first fall: obtaining third measurements of movement of the subject; and processing the third movement measurements to determine if the subject has fallen.

In these embodiments the method further comprises, on detecting the first fall of the subject, obtaining fourth measurements of movement of the subject; processing the fourth movement measurements to determine if the subject stands up before the expiry of a revocation period; performing the fall alert action for the first fall if the subject does not stand up before the expiry of the revocation period; and revoking the fall alert for the first fall if the subject stands up before the expiry of the revocation period.

In some embodiments, prior to the step of obtaining first measurements of movements of the subject, the method further comprises: issuing a prompt to the subject requesting the subject perform a mobility action; and the step of obtaining first measurements of the movements is performed while the subject is performing the mobility action. In this way, the subject may be prompted to perform a mobility action that enables the mobility characteristic to be measured (e.g. if the mobility characteristic relates to a specific type of movement, such as walking a certain distance), and/or to be measured in a way that enables the first value of the mobility characteristic to be reliably compared to the second value of the mobility characteristic (e.g. if the second value was obtained when the subject was performing that mobility action). In these embodiments the mobility action can comprise walking a minimum distance and/or performing a sit-to-stand movement.

In some embodiments the at least one mobility characteristic is related to: the subject's gait, the subject's gait symmetry, the subject's gait irregularity, the subject's stride length, or the subject's balance.

According to a second aspect, there is provided a computer program product comprising computer readable code embodied therein, the code being configured such that, on execution by a suitable computer or processor, the computer or processor is caused to perform the method according to the first aspect or any embodiment thereof.

According to a third aspect, there is provided an apparatus for monitoring a subject. The apparatus comprises a processing unit that is configured to: following detection of a first fall of the subject and a revocation of a fall alert for the first fall due to detecting the subject has stood up after the first fall, obtain first measurements of movement of the subject; determine a first value of at least one mobility characteristic of the subject from the obtained first movement measurements; determine if the mobility of the subject has degraded after the first fall based on the first value of the at least one mobility characteristic and a second value of the at least one mobility characteristic, wherein the second value is determined from second movement measurements obtained prior to the first fall; and, in response to determining that the mobility of the subject has degraded after the first fall, perform a fall alert action in respect of the first fall. Thus, this aspect provides that assistance can still be requested for the subject following a revoked fall alert if the movements of the subject show a degradation following the fall.

In some embodiments the processing unit is configured to perform a fall alert action by issuing an alert to request assistance for the subject. In this way assistance can be automatically requested for the subject. In these embodiments an alert can comprise at least one of an audible alarm, placing a call to a call centre, emergency service or nominated recipient, or sending data to a call centre, emergency service or nominated recipient.

In alternative embodiments, the processing unit is configured to perform a fall alert action by issuing a prompt to the subject to trigger an alert that the subject has fallen and/or that the subject requires assistance. In this way the decision on whether to request assistance remains with the subject, but the prompt may encourage the subject to request assistance.

In some embodiments the processing unit is configured to determine if the mobility of the subject has degraded after the first fall by determining the difference between the first value of the at least one mobility characteristic and the second value of the at least one mobility characteristic; and determining that the mobility of the subject has degraded if the difference between the first value of the at least one mobility characteristic and the second value of the at least one mobility characteristic is more than a threshold amount.

In some embodiments the second value for the at least one mobility characteristic represents a normal value for the at least one mobility characteristic. Thus, the first aspect determines if the subject's movements after the fall have degraded relative to the subject's typical movement ability.

In some embodiments the processing unit is further configured to, prior to detection of the first fall: obtain third measurements of movement of the subject; and process the third movement measurements to determine if the subject has fallen.

In these embodiments the processing unit is further configured to, on detecting the first fall of the subject, obtain fourth measurements of movement of the subject; process the fourth movement measurements to determine if the subject stands up before the expiry of a revocation period; perform the fall alert action for the first fall if the subject does not stand up before the expiry of the revocation period; and revoke the fall alert for the first fall if the subject stands up before the expiry of the revocation period.

In some embodiments, the processing unit is further configured to, prior to obtaining first measurements of movements of the subject, issue a prompt to the subject requesting the subject perform a mobility action; and the processing unit is configured to obtain the first measurements of the movements while the subject is performing the mobility action. In this way, the subject may be prompted to perform a mobility action that enables the mobility characteristic to be measured (e.g. if the mobility characteristic relates to a specific type of movement, such as walking a certain distance), and/or to be measured in a way that enables the first value of the mobility characteristic to be reliably compared to the second value of the mobility characteristic (e.g. if the second value was obtained when the subject was performing that mobility action). In these embodiments the mobility action can comprise walking a minimum distance and/or performing a sit-to-stand movement.

In some embodiments the at least one mobility characteristic is related to: the subject's gait, the subject's gait symmetry, the subject's gait irregularity, the subject's stride length, or the subject's balance.

In some embodiments the processing unit is configured to obtain the first measurements of movement of the subject from a sensor.

According to a fourth aspect, there is provided a system for monitoring a subject. The system comprises a device that is to be worn or carried by a subject and that comprises a sensor for generating first measurements of movement of the subject; and an apparatus as according to the third aspect or any embodiment thereof.

In some embodiments the apparatus is part of the device. In alternative embodiments, the apparatus is separate from the device.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

As noted above, it is desirable to provide techniques that facilitate assistance being requested for a person in case they are injured following a fall.

Figure 1:
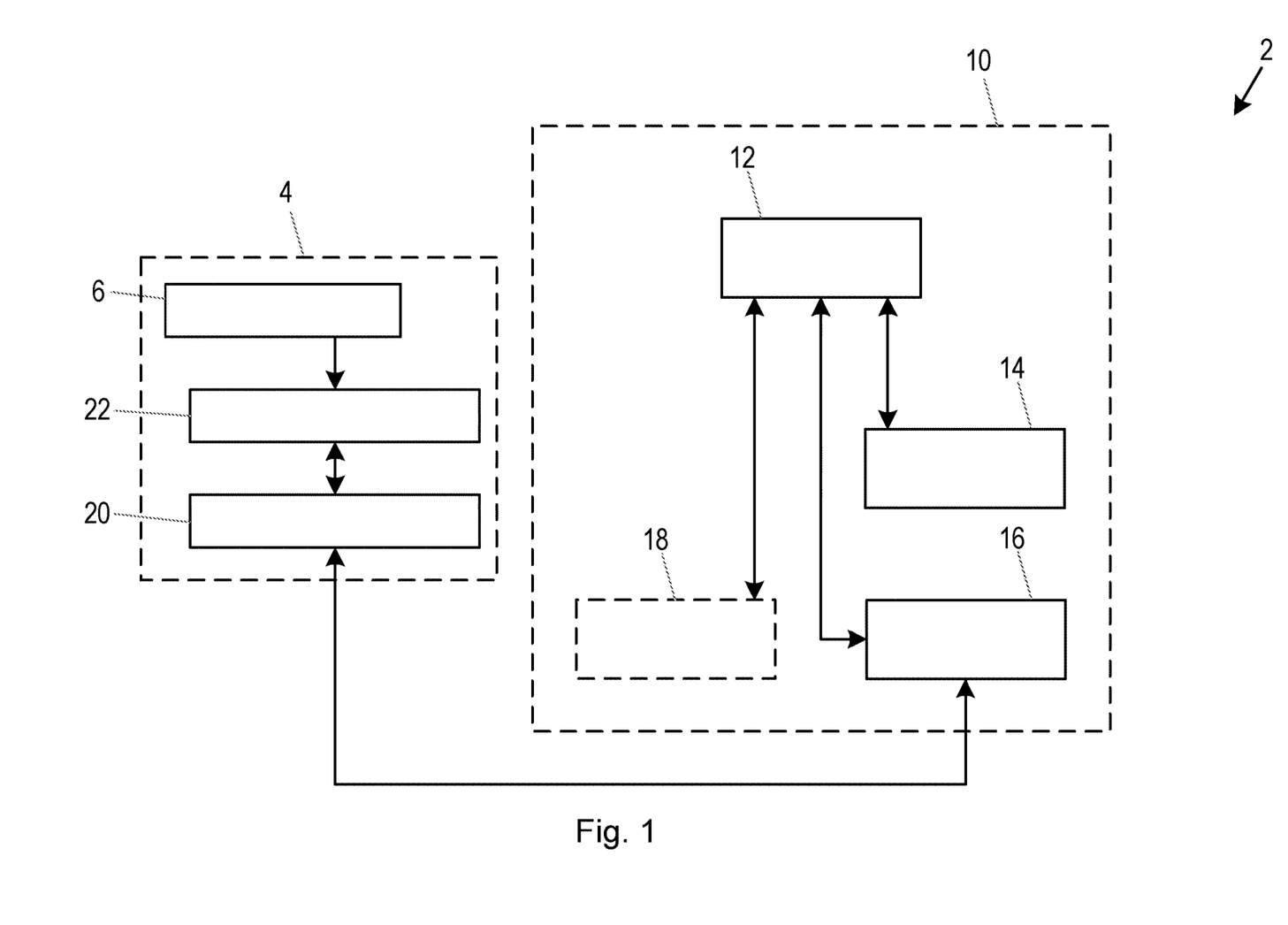
FIG. 1 is a block diagram illustrating a system comprising an apparatus and device according to an exemplary embodiment.

FIG. 1 illustrates a system 2 according to an exemplary embodiment of the teachings presented herein. In this embodiment the system 2 comprises a device 4 that is carried or worn by the subject and that includes a sensor 6 for measuring movement of the subject over time. In further embodiments, the device 4 can include further sensors for measuring movement of the subject over time in addition to the sensor 6.

The sensor 6 generates and outputs a respective signal representing measurements of the movement of the subject over time. Each measurement signal can comprise a time series of measurements (samples), and the measurement signal can therefore relate to the measurements in a time period. The sensor 6 can use any desired sampling frequency, for example 50 measurements per second (50 Hz), 64 Hz or 100 Hz. Different sensors may run at different sampling rates. For example, another sensor may be sampled at 2 Hz, or 4 Hz, or 0.4 Hz, or 1 Hz.

The sensor 6 in the system is a sensor that may directly or indirectly measure the movements of the subject over time. For example, the sensor 6 can be any of an accelerometer, an air pressure sensor, a magnetometer, a gyroscope, a satellite positioning system (SPS) receiver (e.g. a GPS receiver, a GLONASS receiver, a Galileo positioning system receiver, etc.), and a pressure sensor that can be positioned in the subject's shoe (or in each shoe) or other footwear to measure the pressure that the foot is applying to the ground (since these measurements can be indicative of footsteps). In preferred embodiments the sensor 6 is an accelerometer. A sensor that directly or indirectly measures the movements of the subject over time is referred to herein as a "movement sensor", and the movement sensor outputs a "movement signal" representing "movement measurements". A value of at least one mobility characteristic of the subject may be determined from the output "movement measurements" of the sensor 6.

It will be appreciated that the system 2 (and particularly device 4) can include one or more sensors that measure physiological characteristics of the subject, and such sensor(s) can be provided in addition to the movement sensor 6. For example, a skin conductivity sensor can be used to provide measurements of skin conductivity that can be evaluated by a fall detection algorithm to determine if the subject is experiencing a stress response (for example which could be expected following a fall). Similarly, a photoplethysmography (PPG) sensor can be used to provide measurements of blood volume over time at the PPG sensor location on the body, with the PPG signal representing a subject's pulse or heartbeat. The PPG signal can also be evaluated by a fall detection algorithm to determine if the subject is experiencing a stress response, or by a walking detection or assessment algorithm to determine if the subject is physically exerting themselves or is generally inactive (e.g. sedentary). Those skilled in the art will be aware of other types of physiological characteristic sensors that can be used in evaluating the movement of a subject as part of the fall detection algorithm.

In the case of the sensor 6 being an accelerometer, the accelerometer can generate and output a movement signal that contains a plurality of acceleration measurement samples representing the movements of the subject at a plurality of time instants. The accelerometer is typically an accelerometer that measures accelerations in three dimensions, and the movement signal generated by the accelerometer can include respective measurements representing the accelerations in each of the three dimensions. For example, the accelerometer can output respective measurement signals for each of an x-axis, y-axis and z-axis of a Cartesian coordinate system.

In the case of the sensor 6 being a gyroscope, the gyroscope can generate and output a movement signal that contains a plurality of gyroscope measurement samples representing the rotational movement and/or orientation of the subject at a plurality of time instants.

In the case of the sensor 6 being an air pressure sensor, the air pressure sensor can include any type of sensor for measuring air pressure or changes in air pressure. The air pressure sensor can generate and output an air pressure signal representing measurements of air pressure or changes in air pressure at the air pressure sensor. The air pressure signal can comprise a time series of air pressure measurements (samples) and the air pressure signal can therefore relate to the air pressure or changes in air pressure in a time period. The air pressure sensor can use any desired sampling frequency, for example 1 Hz or 50 Hz. In other embodiments a microphone might be used. Typically, the microphone is sampled at 16 kHz or higher frequencies.

Returning to FIG. 1, the system 2 also comprises an apparatus 10 that receives the sensor measurements or measurement signals from the sensor 6 in the device 4 and analyses the measurements or signal to monitor the subject according to the techniques described herein. in some embodiments the apparatus 10 may also analyse the measurements or signal to evaluate the movement of the subject, e.g. to detect a fall, to determine a fall risk, or evaluate a walking ability and walking quality of the subject.

The device 4 can be in any form suitable enabling the subject to carry or wear the device 4. For example, the device 4 may be in the form of a watch or smartwatch, a smartphone, a bracelet, a pendant, a necklace, a chest band, integrated into an item of clothing, etc. In some embodiments, as shown in FIG. 1, the apparatus 10 can be separate from the device 4. In these embodiments, the apparatus 10 can be any type of electronic device or computing device that can communicate with, or otherwise receive the measurements or sensor signal(s) directly or indirectly from, the device 4. For example the apparatus 10 can be, or be part of, a computer, a laptop, a tablet, a smartphone, a smartwatch, etc., and as such may be an apparatus that is present or used in the home or care environment of the subject. In other implementations, the apparatus 10 can be an apparatus that is remote from the subject, and remote from the home or care environment of the subject. For example, the apparatus 10 can be a server, for example a server in a data centre (also referred to as being 'in the cloud'). In alternative embodiments, the apparatus 10 (and in particular the functionality of the apparatus 10 as described herein) can be integral with the device 4. Therefore the apparatus 10 can also be carried or worn by the subject as part of the device 4.

The apparatus 10 includes a processing unit 12 that controls the operation of the apparatus 10 and that can be configured to execute or perform the methods described herein. In particular, the processing unit 12 can obtain the measurements/signal(s) and process them to monitor the subject. The processing unit 12 can be implemented in numerous ways, with software and/or hardware, to perform the various functions described herein. The processing unit 12 may comprise one or more microprocessors or digital signal processor (DSPs) that may be programmed using software or computer program code to perform the required functions and/or to control components of the processing unit 12 to effect the required functions. The processing unit 12 may be implemented as a combination of dedicated hardware to perform some functions (e.g. amplifiers, preamplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), and field-programmable gate arrays (FPGAs).

The processing unit 12 is connected to a memory unit 14 that can store data, information and/or signals (including movement measurements) for use by the processing unit 12 in controlling the operation of the apparatus 10 and/or in executing or performing the methods described herein. In some implementations the memory unit 14 stores computer-readable code that can be executed by the processing unit 12 so that the processing unit 12 performs one or more functions, including the methods described herein. In particular embodiments, the program code can be in the form of an application for a smartwatch, a smartphone, tablet, laptop or computer. The memory unit 14 can comprise any type of non-transitory machine-readable medium, such as cache or system memory including volatile and non-volatile computer memory such as random access memory (RAM) static RAM (SRAM), dynamic RAM (DRAM), read-only memory (ROM), programmable ROM (PROM), erasable PROM (EPROM) and electrically erasable PROM (EEPROM), implemented in the form of a memory chip, an optical disk (such as a compact disc (CD), a digital versatile disc (DVD) or a Blu-Ray disc), a hard disk, a tape storage solution, or a solid state device, including a memory stick, a solid state drive (SSD), a memory card, etc.

In the embodiment of the system 2 shown in FIG. 1, as the apparatus 10 is separate from the device 4 that includes the sensor 6, the apparatus 10 also includes interface circuitry 16 for enabling a data connection to and/or data exchange with other devices, including device 4, and optionally any one or more of servers, databases, user devices, and other sensors. The connection may be direct or indirect (e.g. via the Internet), and thus the interface circuitry 16 can enable a connection between the apparatus 10 and a network, such as the Internet, or between the apparatus 10 and device 4, via any desirable wired or wireless communication protocol. For example, the interface circuitry 16 can operate using WiFi, Bluetooth, Zigbee, or any cellular communication protocol (including but not limited to Global System for Mobile Communications (GSM), Universal Mobile Telecommunications System (UMTS), Long Term Evolution (LTE), LTE-Advanced, etc.). In the case of a wireless connection, the interface circuitry 16 (and thus apparatus 10) may include one or more suitable antennas for transmitting/receiving over a transmission medium (e.g. the air). Alternatively, in the case of a wireless connection, the interface circuitry 16 may include means (e.g. a connector or plug) to enable the interface circuitry 16 to be connected to one or more suitable antennas external to the apparatus 10 for transmitting/receiving over a transmission medium (e.g. the air). The interface circuitry 16 is connected to the processing unit 12 to enable information or data received by the interface circuitry 16 to be provided to the processing unit 12, and/or information or data from the processing unit 12 to be transmitted by the interface circuitry 16.

The interface circuitry 16 can be used to receive measurements/signal generated by the sensor 6, and any further sensor(s) (if present in the system 2).

In some embodiments, the interface circuitry 16 can be used to output a result of the processing by the processing unit 12, for example an indication of the evaluation of the movement of the subject (e.g. an indication that the subject has suffered a fall).

In some embodiments, the apparatus 10 comprises a user interface 18 that includes one or more components that enables a user of apparatus 10 (e.g. the subject, or a care provider for the subject) to input information, data and/or commands into the apparatus 10 (e.g. for starting or enabling the monitoring of the subject according to the techniques described herein), and/or enables the apparatus 10 to output information or data to the subject or other user of the apparatus 10. An output may be an audible, visible and/or tactile indication, for example a fall alert or a prompt for the subject to request assistance. The user interface 18 can comprise any suitable input component(s), including but not limited to a keyboard, keypad, one or more buttons, switches or dials, a mouse, a track pad, a touchscreen, a stylus, a camera, a microphone, etc., and the user interface 18 can comprise any suitable output component(s), including but not limited to a display screen, one or more lights or light elements, one or more loudspeakers, a vibrating element, etc.

It will be appreciated that a practical implementation of apparatus 10 may include additional components to those shown in FIG. 1. For example the apparatus 10 may also include a power supply, such as a battery, or components for enabling the apparatus 10 to be connected to a mains power supply.

As noted above, the sensor 6 is part of device 4, which is separate from the apparatus 10 in the embodiment shown in FIG. 1. In order for the measurements/signal(s) to be communicated from the device 4 to the apparatus 10, the device 4 comprises interface circuitry 20. The interface circuitry 20 may be implemented in a similar way to the interface circuitry 16 in the apparatus 10.

In some embodiments, the device 4 can also include a processing unit 22 for controlling the operation of the device 4. This processing unit 22 can also be used to perform some pre-processing of the measurements/signal(s) before they are communicated to the apparatus 10, for example the measurements can be filtered to reduce or remove a noise component or artefacts. The processing unit 22 may be implemented in a similar way to the processing unit 12 in the apparatus 10.

It will be appreciated that a practical implementation of device 4 may include additional components to those shown in FIG. 1. For example the device 4 may also include a power supply, preferably a battery so that the device 4 is portable, or components for enabling the device 4 to be connected to a mains power supply.

In alternative embodiments of the system 2 where the apparatus 10 is part of the device 4, it will be appreciated that only one processing unit 12/22 may be present, and interface circuitry is not required to communicate the measurements/signal(s) to the processing unit 12.

As noted above, after a fall is detected, a revocation period is started before a fall alert is issued in which the subject is monitored to determine if they stand up. A fall alert can be revoked (i.e. not sent or not issued) based on the detection that the subject has stood up following the detected fall before the expiry of the revocation period. However, it has been recognised that the fact that a subject has stood up following a fall does not necessarily mean that the subject is uninjured and does not require assistance.

To address this issue, the techniques proposed herein provide an approach that makes use of mobility-related measurements to improve the monitoring of a subject that has stood up following a detected fall but may still require assistance.

Briefly, according to the techniques described herein, following detection of a first fall of the subject and a revocation of a fall alert for the first fall due to detecting the subject has stood up after the first fall, first measurements of movement of the subject are obtained. The first measurements may be obtained by the sensor 6. A first value of at least one mobility characteristic of the subject is determined from the obtained first movement measurements. The first value of the at least one mobility characteristic may be determined by the processing unit 12. It is then determined if the mobility of the subject has degraded after the first fall based on the first value of the at least one mobility characteristic and a second value of the at least one mobility characteristic that is (or was) determined from second movement measurements obtained prior to the first fall. The second measurements may have been obtained by the sensor 6. The second value of the at least one mobility characteristic may be determined by the processing unit 12 or retrieved from a memory (e.g. memory unit 14). The second value may be determined before or after the fall was detected. In response to determining that the mobility of the subject has degraded after the first fall (i.e. the mobility of the subject is worse after the fall), a fall alert action in respect of the first fall is performed. The fall alert action in respect of the first fall may be performed by the processing unit 12.

General embodiments of the techniques presented herein for monitoring a subject are described below with reference to the flow chart in FIG. 2.

Figure 2:
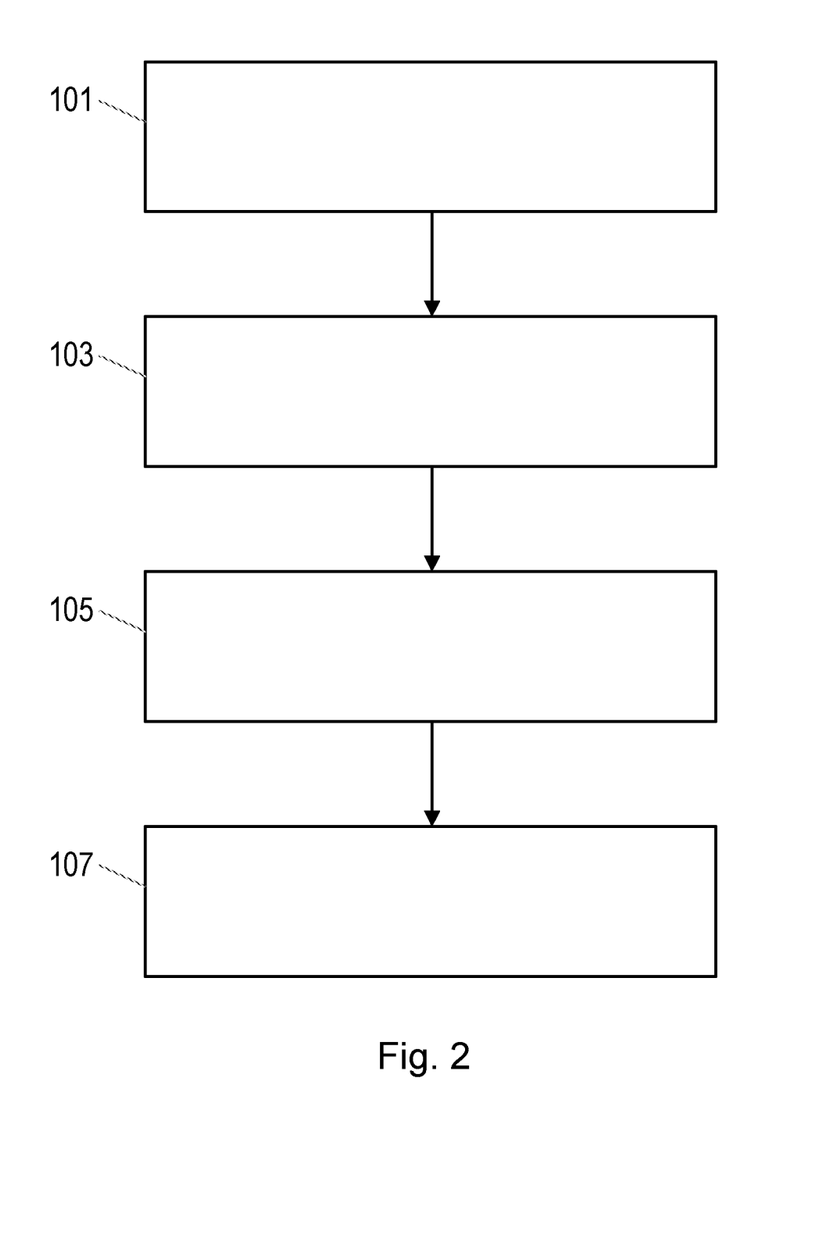
FIG. 2 is a flow chart illustrating a method according to an exemplary embodiment.

One or more of the steps of the method of FIG. 2 can be performed by the processing unit 12 in the apparatus 10, in conjunction with any of the sensor 6, memory unit 14, interface circuitry 16 and user interface 18 as appropriate. The processing unit 12 may perform the one or more steps in response to executing computer program code, that can be stored on a computer readable medium, such as, for example, the memory unit 14.

In a first step, step 101, following detection that the subject has fallen (which is referred to herein as a "first fall") and a revocation of a fall alert for the first fall due to detecting the subject has stood up before the revocation period expired, the processing unit 12 obtains first measurements of the movement of the subject from a sensor 6. The sensor 6 is in device 4, and the device 4 is carried or worn by the subject as the sensor 6 measures the subject. The measurements of the subject relate to the subject during at least a first time period following the revocation of the fall alert. In this step, the processing unit 12 can obtain the first measurements directly from the sensor 6 or indirectly from the sensor 6 (e.g. via interface circuitry 16 and interface circuitry 20). In these embodiments the processing unit 12 may be able to process the measurements as they are received (e.g. in real-time or near-real-time) to monitor the subject in real time or after a short delay (e.g. a few seconds). The first time period may have any suitable duration, and should be long enough to enable measurements to be obtained for assessing the mobility of the subject. For example the first time period can be at least 5 seconds (s), at least 10 s, at least 20 s, at least 1 minute, or at least 5 minutes.

In step 103, a first value of at least one mobility characteristic of the subject is determined from the obtained first movement measurements. The processing unit 12 may determine the first value of the at least one mobility characteristic of the subject.

The value of the mobility characteristic is to be used as an indicator of the mobility of the subject, and therefore the at least one mobility characteristic can be related to or a measure of any one or more of: the subject's gait, the subject's gait symmetry, the subject's gait irregularity, the subject's stride length, or the subject's balance. In some embodiments, the mobility characteristic can be any of walking speed, time taken to walk a certain distance (e.g. 10 metres), sway (which is the amount of lateral displacement while walking), stride length, variance (e.g. of stride length), the time taken to perform a sit-to-stand (STS) movement, or a combination of two or more of the above characteristics, for example the time to perform a STS movement and walk a certain distance.

It will be appreciated that the processing unit 12 may determine any of the aforementioned mobility characteristics from the first movement measurements obtained by the sensor 6 by processing the first movement measurements in a number of different ways, and generally, those skilled in the art will be aware of numerous techniques for identifying the aforementioned mobility characteristics from first movement measurements mentioned above.

In some embodiments, the at least one mobility characteristic may be an overall mobility score for the subject. A mobility score can be directly derived from a mobility characteristic (e.g. from walking speed in metres/second, m/s), by a non-linear derivation (e.g. score=1 if walking speed<1 m/s, score=2 if walking speed>1 m/s), by a weighted (or non-weighted) average of several mobility characteristics (e.g. by linear regression), a non-linear combination of mobility characteristics (e.g. score=3 if walking speed>1 m/s and sway<10 cm), or derived through machine learning (e.g. deep learning, gradient boosting) where mobility characteristics serve as inputs. Scores can also (in a similar manner) be derived from features of mobility characteristics, e.g. declining slope or decrease in walking speed over time.

In some embodiments, in step 103 values of a plurality of mobility characteristics can be determined from the first movement measurements.

Thus, the value of the at least one mobility characteristic that is determined from the first movement measurements can provide an indication of the quality of the mobility of the subject after standing up following the first fall.

In step 105, it is determined if the mobility of the subject has degraded after the first fall based on the first value of the at least one mobility characteristic and a second value of the at least one mobility characteristic that relates to the subject prior to the first fall. The second value is determined from second movement measurements that were obtained prior to the first fall (and indeed the second value itself may have been determined prior to the first fall).

It will be appreciated that the second measurements of movement of the subject may have been obtained in a similar manner to the first measurements of movement of the subject, as described above. For example, the processing unit 12 may have obtained second measurements of the movement of the subject from the sensor 6.

It will also be appreciated that the second value of the at least one mobility characteristic may have been determined from the second movement measurements in a similar manner that the first value of the at least one mobility characteristic is determined from the first movement measurements, as described above.

It will be appreciated that as the second movement measurements relate to a time period prior to the first fall, the second movement measurements are likely to relate to movements and a mobility level that is considered normal for the subject. Thus, the value of the at least one mobility characteristic that is determined from the second movement measurements will likely be representative of a normal value for the at least one mobility characteristic for the subject.

Thus, in step 105 if the first value of a mobility characteristic determined from movement measurements obtained following the first fall differs from the second value of the mobility characteristic determined from movement measurements obtained prior to the first fall, then this may be indicative that the mobility of the subject has degraded following the fall, in particular if the first value indicates a poorer or worse mobility after the fall than prior to the fall. It will be appreciated that a degradation in the mobility of the subject may result from the subject being confused, disorientated, and/or sustaining an injury of some kind from the fall. It will also be appreciated that the confusion, disorientation and/or injury may have been the direct cause or a contributory factor to the occurrence of the first fall.

In some embodiments, the second movement measurements may have been obtained from any suitable period of time preceding the first fall. The time period (which is referred to herein as a 'second time period') may have any suitable duration, and should be long enough to enable measurements to be obtained for assessing the mobility of the subject. The second time period may have the same duration as the first time period, or be shorter or longer. As an example the second time period can be at least 5 s, at least 10 s, at least 20 s, at least 1 minute, or at least 5 minutes.

In some embodiments, the second movement measurements may be obtained from a period of time that was not immediately before the first fall. As noted above, in the period of time that directly precedes the first fall, the subject may have been experiencing disorientation or confusion, and thus the movement of the subject within the directly preceding period may not have been representative of the typical, or the normal, movement of the subject.

In embodiments where higher values of the mobility characteristic are indicative of better mobility, degradation in the mobility of the subject may be indicated by a decrease in the value of the mobility characteristic across the first fall. For example, a decrease in a value of a mobility characteristic that is a measure of the subject's balance may be indicative of degradation in the mobility of the subject.

In embodiments where lower values of the mobility characteristic are indicative of better mobility, degradation in the mobility of the subject may be indicated by an increase in the value of the mobility characteristic across the fall. For example, an increase in a value of a mobility characteristic that is a measure of the subject's gait irregularity may be indicative of degradation in the mobility of the subject.

In some embodiments, the step of determining if the mobility of the subject has degraded after the first fall comprises determining the difference between the first value of the at least one mobility characteristic and the second value of the at least one mobility characteristic, and determining that the mobility of the subject has degraded if the difference between the first value of the at least one mobility characteristic and the second value of the at least one mobility characteristic is more than a threshold amount, and the difference is a worsening of the mobility of the subject.

In some embodiments, it may be determined that the mobility of the subject has degraded if the difference between the first value of the at least one mobility characteristic and the second value of the at least one mobility characteristic is more than a predefined percentage of the second value, and the difference is a worsening of the mobility of the subject. For example, it may be determined that the mobility of the subject has degraded if the difference between the first value of the at least one mobility characteristic and the second value of the at least one mobility characteristic is more than 10% of the second value, and the difference is a worsening of the mobility of the subject. However, it will be appreciated that any suitable percentage may be selected.

In embodiments where values for multiple mobility characteristics are determined, rather than compare individual pre- and post-fall values for each mobility characteristic, machine learning techniques (for example, linear regression or deep neural networks) may be used to determine if the mobility of the subject has degraded after the first fall based on the values of the mobility characteristics before and after the fall.

In response to determining in step 105 that the mobility of the subject has degraded after the first fall, in step 107, a fall alert action is performed in respect of the first fall.

In some embodiments, the step of performing a fall alert action comprises issuing an alert to request assistance for the subject. The alert may be issued via the interface circuitry 16 or the user interface 18 as appropriate. An alert to request assistance may comprise at least one of an audible alarm, placing a call to a call centre, emergency service or nominated recipient, or sending data to a call centre, emergency service or nominated recipient. In some examples, the alert to request assistance for the subject may therefore provide an indication that the subject has fallen (i.e. it is a fall alert). In other examples, the alert may provide an indication that the subject has stood up following a fall, but may still require assistance. For example, the alert may provide an indication that the mobility of the subject has degraded following a fall. In some embodiments, an indication of the degradation of the subject's mobility may be provided alongside, or as part of, the alert. For example, the first value of the mobility characteristic, and also the second value of the mobility characteristic may be transmitted as data to a call centre, emergency service or nominated recipient. In other examples, the alert may provide an indication that the subject is disorientated and/or confused and/or injured following a fall.

In some embodiments, the fall alert action comprises issuing a prompt to the subject to trigger an alert that they have fallen. In some embodiments, this prompt may be a voice prompt (e.g. a spoken message) and/or a visual prompt (e.g. a light, a written message on a display screen). In some embodiments, the issued prompt may also comprise an indication to the subject that their mobility has degraded following the fall. In some embodiments, an indication of the aspect of the subject's mobility that has degraded may be provided alongside, or as part of, the prompt.

In some embodiments, the fall alert action comprises issuing a prompt to the subject indicating that they require assistance. In some embodiments, this prompt may be a voice prompt (e.g. a spoken message) and/or a visual prompt (e.g. a light, a written message on a display screen). In some embodiments, the issued prompt may also comprise an indication to the subject that their mobility has degraded following the fall. For example, an indication of the aspect of the subject's mobility that has degraded may be provided alongside, or as part of, the prompt.

Thus, if it is determined that the mobility of the subject has degraded following a fall, it is determined that the subject may need further assistance, and an alert to request assistance for the subject can still be generated, despite the earlier revocation of the fall alert. This alert can either be generated automatically by the apparatus 10, or by prompting the subject to request assistance, e.g. by pressing a personal help button.

If it is determined in step 105 that the mobility of the subject has not degraded after the first fall (or not degraded by a sufficient amount, e.g. if any degradation is less than a required threshold amount), then no fall alert action is performed in respect of the first fall. Thus, no audible alarm is triggered, no call is placed to another party, no data is sent to another party, and a prompt to request assistance is not provided to the subject.

In some embodiments, the apparatus 10 does not implement the fall detection algorithm or check to determine if the subject stands up before the revocation period expires. The fall detection algorithm and revocation period check can be implemented by a separate device, apparatus or system, and the operation of the apparatus 10 as described with reference to FIG. 2 can be triggered by the apparatus 10 receiving an indication from that separate device, apparatus or system that the subject has fallen but stood up before the expiry of the revocation period.

In alternative embodiments, the apparatus 10 also implements the fall detection algorithm that evaluates the movements of the subject (e.g. as measured by sensor 6) with the aim of detecting whether the subject has suffered a fall. In these embodiments, on detecting a fall the apparatus 10 can also initiate the revocation period and evaluate the movements of the subject (e.g. as measured by sensor 6) to determine if the subject stands up before the revocation period expires. If the revocation period expires before the subject stands up, the apparatus 10 can trigger a fall alert, for example by triggering or generating an audible alarm, placing a call to a call centre, emergency service or nominated recipient, or sending data to a call centre, emergency service or nominated recipient. If the subject stands up before the expiry of the revocation period, the apparatus 10 can then initiate the method shown in FIG. 2 starting with step 101.

More specifically, in the embodiments where the apparatus 10 implements the fall detection algorithm, the method in FIG. 2 can further comprise, prior to step 101 and prior to detection of a fall, obtaining measurements of movement of the subject (these measurements are referred to herein as 'third measurements'). The third measurements of movement of the subject may be obtained in a similar manner to the measurements of movement of the subject obtained in step 101, as described above. For example, the processing unit 12 may obtain the third measurements of the movement of the subject from the sensor 6. The processing unit 12 can then process the third movement measurements to determine if the subject has fallen. In embodiments where the sensor 6 is an accelerometer, the processing unit 12 may determine that the subject has fallen from acceleration measurements by processing the acceleration measurements in a number of different ways, e.g. by detecting an impact, a free-fall, an orientation change, etc. In embodiments where the sensor 6 is an air pressure sensor, the processing unit 12 may determine that the subject has fallen from air pressure measurements by processing the air pressure measurements in a number of different ways, e.g. by detecting an altitude decrease with a magnitude consistent with a fall. Those skilled in the art will be aware of numerous techniques for determining that a subject has fallen from measurements of movement of the subject.

If a fall by the subject is detected, the revocation period can be started. As noted above the revocation period allows time for the subject to get up following the detected fall before a fall alert is triggered or generated. The revocation period can typically be 30 seconds to 2 minutes long, although other suitable durations can be used. During the revocation period, the movements of the subject are analysed to determine if the subject stands up. Thus after detecting a fall, the method (still prior to step 101) further comprises obtaining further measurements of movement of the subject (these measurements are referred to as 'fourth measurements'). These measurements of movement of the subject may be obtained in the revocation period, and obtained in a similar manner to the measurements of movement of the subject obtained in step 101 (e.g. using the sensor 6). These movement measurements are processed to determine if the subject stands up before the expiry of the revocation period. In embodiments where the sensor 6 is an accelerometer, the processing unit 12 may determine that the subject has stood up by processing the acceleration measurements in a number of different ways, e.g. by detecting an orientation change, walking movements, vertical acceleration, etc. In embodiments where the sensor 6 is an air pressure sensor, the processing unit 12 may determine that the subject has stood up by processing the air pressure measurements in a number of different ways, e.g. by detecting an altitude increase consistent with the subject standing up. Those skilled in the art will be aware of numerous techniques for determining whether a subject has stood up from measurements of movement of the subject.

If the subject does not stand up by the time that the revocation period expires, the processing unit 12 can perform a fall alert action for the fall. The fall alert action can be, for example, triggering or generating an audible alarm, placing a call to a call centre, emergency service or nominated recipient, or sending data to a call centre, emergency service or nominated recipient.

If the subject does stand up before the revocation period expires, the processing unit 12 does not perform a fall alert action (i.e. so no audible alarm is generated and no call is placed to another party, etc.), and step 101 of FIG. 2 is initiated.

In some embodiments, to improve the reliability of the mobility evaluation performed in step 105, the subject may be asked to perform a particular mobility action, e.g. a movement such as walking, so that the mobility characteristic can be obtained. Thus, prior to step 101 (but after detecting that the subject has stood up), the method can further comprise issuing a prompt to the subject to request the subject perform a specified mobility action. The mobility action may comprise any of the following: walking a minimum distance, running a minimum distance, standing up, sitting down, standing up from sitting on a chair (known as a sit-to-stand (STS) movement), ascending stairs or descending stairs. It will be appreciated that mobility actions such as walking or running can provide an indication of the subject's gait, stride length, stride regularity, etc. It will also be appreciated that mobility actions such as standing up, sitting down or standing up from sitting on a chair (known as a sit-to-stand (STS) movement) can provide an indication of the subject's balance, or the subject's stability. After issuing the prompt to perform the mobility action, step 101 can be performed while the subject is performing the mobility action. Thus, for example, the first measurements of the movement may be obtained while the subject is walking a minimum distance or while the subject is standing up (standing still).

In some embodiments, for example during a calibration procedure for the apparatus 10, or periodically as the apparatus 10 is being used by the subject, the apparatus 10 can issue a prompt to the subject from time to time to perform the mobility action so that a value for the mobility characteristic for the subject can be determined or updated. This value of the mobility characteristic is the second value of the mobility characteristic that is used in step 105. Thus, for example, after issuing a prompt to the subject to request the subject perform the specified mobility action, the second measurements of the movement of the subject can be obtained and the second value of the mobility characteristic determined.

Therefore there is provided techniques that provide improvements in the monitoring of a subject that has stood up following a detected fall but may still require assistance.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method of monitoring a subject, the method comprising:
    following detection of a first fall of the subject and a revocation of a fall alert for the first fall due to detecting the subject has stood up after the first fall, obtaining first measurements of movement of the subject, by a device that is to be worn by a subject and that comprises a sensor for generating first measurements of movement of the subject;
    determining, by the device, a first value of at least one mobility characteristic of the subject from the obtained first movement measurements;
    determining, by the device, if the mobility of the subject has degraded after the first fall based on the first value of the at least one mobility characteristic and a second value of the at least one mobility characteristic, wherein the second value is determined from second movement measurements obtained prior to the first fall; and
    in response to determining that the mobility of the subject has degraded after the first fall, by the device, performing a fall alert action in respect of the first fall.

2. A method as claimed in claim 1, wherein the step of performing a fall alert action comprises:
    issuing an alert to request assistance for the subject.

3. A method as claimed in claim 2, wherein an alert comprises at least one of an audible alarm, placing a call to a call center, emergency service, or nominated recipient, or sending data to a call center, emergency service, or nominated recipient.

4. A method as claimed in claim 1, wherein the step of performing a fall alert action, comprises:
    issuing a prompt to the subject to trigger an alert that the subject has fallen and/or that the subject requires assistance.

5. A method as claimed in claim 1, wherein the step of determining if the mobility of the subject has degraded after the first fall comprises:
    determining the difference between the first value of the at least one mobility characteristic and the second value of the at least one mobility characteristic; and
    determining that the mobility of the subject has degraded if the difference between the first value of the at least one mobility characteristic and the second value of the at least one mobility characteristic is more than a threshold amount.

6. A method as claimed in claim 1, wherein the second value for the at least one mobility characteristic represents a normal value for the at least one mobility characteristic.

7. A method as claimed in claim 1, wherein prior to the step of obtaining first measurements of movements of the subject, the method further comprises:
    issuing a prompt to the subject requesting the subject perform a mobility action; and
    wherein the step of obtaining first measurements of the movements is performed while the subject is performing the mobility action.

8. A non-transitory computer readable storage medium storing computer readable code, the code being configured such that, on execution by a suitable computer or processor in a device that is to be worn by a subject and that comprises a sensor for generating first measurements of movement of the subject, the computer or processor is caused to perform the method as claimed in claim 1.

9. An apparatus for monitoring a subject, comprising:
a processing unit, in a device that is to be worn by a subject and that comprises a sensor for generating first measurements of movement of the subject, that is configured to:
following detection of a first fall of the subject and a revocation of a fall alert for the first fall due to detecting the subject has stood up after the first fall, obtain first measurements of movement of the subject, by the device;
determine a first value of at least one mobility characteristic of the subject from the obtained first movement measurements, by a device;
determine if the mobility of the subject has degraded after the first fall based on the first value of the at least one mobility characteristic and a second value of the at least one mobility characteristic, by the device, wherein the second value is determined from second movement measurements obtained prior to the first fall; and
in response to determining, by the device, that the mobility of the subject has degraded after the first fall, perform a fall alert action in respect of the first fall.

10. An apparatus as claimed in claim 9, wherein the processing unit is configured to perform a fall alert action by:
issuing an alert to request assistance for the subject.

11. An apparatus as claimed in claim 9, wherein the processing unit is configured to perform a fall alert action by:
issuing a prompt to the subject to trigger an alert that the subject has fallen and/or that the subject requires assistance.

12. An apparatus as claimed in claim 9, wherein the processing unit is configured to determine if the mobility of the subject has degraded after the first fall by:
determining the difference between the first value of the at least one mobility characteristic and the second value of the at least one mobility characteristic; and
determining that the mobility of the subject has degraded if the difference between the first value of the at least one mobility characteristic and the second value of the at least one mobility characteristic is more than a threshold amount.

13. An apparatus as claimed in claim 9, wherein the second value for the at least one mobility characteristic represents a normal value for the at least one mobility characteristic.

14. An apparatus as claimed in claim 9, wherein the processing unit is further configured to, prior to obtaining the first measurements of movements of the subject, issue a prompt to the subject requesting the subject perform a mobility action; and, the processing unit is configured to obtain the first measurements of the movements while the subject is performing the mobility action.

15. A system for monitoring a subject, the system comprising:
a device that is to be worn by a subject and that comprises a sensor for generating first measurements of movement of the subject; and an apparatus as claimed in claim 9.

16. A wearable device to be worn by a subject and that comprises a sensor for generating first measurements of movement of the subject for monitoring a subject, comprising:
a processing unit, in the device, that is configured to:
following detection of a first fall of the subject and a revocation of a fall alert for the first fall due to detecting the subject has stood up after the first fall, by the device, obtain first measurements of movement of the subject;
determine, by the device, a first value of at least one mobility characteristic of the subject from the obtained first movement measurements;
determine, by the device, if the mobility of the subject has degraded after the first fall based on the first value of the at least one mobility characteristic and a second value of the at least one mobility characteristic, wherein the second value is determined from second movement measurements obtained prior to the first fall; and
in response to determining that the mobility of the subject has degraded after the first fall, perform, by the device, a fall alert action in respect of the first fall a sensor configured to generate the second movement measurements of the subject prior to the first fall, and further configured to generate the first measurements of movement of the subject after the first fall;
interface circuitry configured to communicate the fall alert action; and
a power supply configured to power the sensor and the interface circuitry.

17. The apparatus of claim 16, wherein the sensor comprises an accelerometer, an air pressure sensor, a magnetometer, a gyroscope, a satellite positioning system receiver, a pressure sensor, a skin conductivity sensor, and/or a photoplethysmography sensor.

18. The apparatus of claim 16, further comprising a memory unit configured to store the second movement measurements of the subject prior to the first fall and/or the determined second value of the at least one mobility characteristic.

* * * * *